United States Patent [19]

Edwards et al.

[11] Patent Number: 5,008,255
[45] Date of Patent: Apr. 16, 1991

[54] METHOD FOR ENHANCING SOLUBILITY OF TRIMETHOPRIM WITH SODIUM SULFACETAMIDE, AND SYNERGISTIC PHARMACEUTICAL COMPOSITIONS DERIVED THEREFROM

[75] Inventors: John G. Edwards, Cleburne; Wesley W. Han; Yusuf Ali, both of Fort Worth, all of Tex.

[73] Assignee: Alcon Laboratories, Inc., Fort Worth, Tex.

[21] Appl. No.: 479,827

[22] Filed: Feb. 14, 1990

Related U.S. Application Data

[63] Continuation of Ser. No. 296,270, Jan. 12, 1989, abandoned, which is a continuation of Ser. No. 96,682, Sep. 14, 1987, abandoned, which is a continuation of Ser. No. 946,344, Dec. 24, 1986, abandoned.

[51] Int. Cl.$^5$ .................... A61K 31/63; A61K 31/505
[52] U.S. Cl. ...................................... 514/155; 514/275
[58] Field of Search ................................ 514/155, 275

[56] References Cited

U.S. PATENT DOCUMENTS 3,985,873 10/1976 Alvan et al. .......................... 514/11

FOREIGN PATENT DOCUMENTS 1582692 1/1981 United Kingdom ................ 514/155

*Primary Examiner*—Jerome D. Goldberg
*Attorney, Agent, or Firm*—James A. Arno; Gregg C. Brown

[57] ABSTRACT

A method of preparing aqueous pharmaceutical compositions containing a synergistic combination of trimethoprim and sodium sulfacetamide is described. The method results in a significant improvement in the aqueous solubility of trimethoprim due to a favorable interaction between the trimethoprim and sodium sulfacetamide which is dependent on a mildly acidic pH.

5 Claims, No Drawings

METHOD FOR ENHANCING SOLUBILITY OF TRIMETHOPRIM WITH SODIUM SULFACETAMIDE, AND SYNERGISTIC PHARMACEUTICAL COMPOSITIONS DERIVED THEREFROM

This is a continuation of patent application Ser. No. 296,270, filed Jan. 12, 1989, now abandoned, which was a continuation of Ser. No. 096,682, filed Sept. 14, 1987, now abandoned, which was a continuation of Ser. No. 946,344, filed Dec. 24, 1986, now abandoned.

BACKGROUND OF THE INVENTION

1. Field of the Invention

The present invention relates to the field of pharmaceutical compositions comprising a synergistic combination of trimethoprim and sodium sulfacetamide. More particularly, this invention relates to aqueous preparations containing trimethoprim and sodium sulfacetamide, wherein the trimethoprim has been solubilized by the sodium sulfacetamide. These preparations are particularly well-suited for ophthalmic or otic use. 2. Discussion of Related Art It is known that trimethoprim, which is classified as a benzylpyrimidine, potentiates the antimicrobial activity of sulfonamides (e.g., sulfamethoxazole). Synergistic combinations of trimethoprim and one or more sulfonamides have been used extensively in the treatment of bacterial infections, particularly systemic infections and infections of the urinary tract. Reference is made to the following publications for further background regarding such compositions: U.S. Pat. Nos. 3,515,783; 3,551,564; 4,303,643; 4,332,796; and 4,386,084.

There have been two significant problems associated with prior art attempts to formulate aqueous pharmaceutical preparations containing either trimethoprim or a combination of trimethoprim and one or more sulfonamides. First, it is well known that trimethoprim has a tendency to form insoluble complexes when combined with sulfonamides in aqueous media. The poor aqueous solubility of trimethoprim represents a second significant problem associated with formulation of such solutions. Prior attempts to address these problems are described in the following patent publications: U.K. Patent Application GB 2,073,587A; U.K. Patent Specification 1,582,692; U.S. Pat. No. 3,985,873; and U.S. Pat. No. 3,985,876. The U.K. patent publications describe the use of aldehydes and high concentrations of polyvinylpyrrolidone, respectively, as solutions to the above-cited formulation problems. U.S. Pat. No. 3,985,873, proposes the use of water soluble mono salts of trimethoprim to overcome the aqueous solubility problem mentioned above. As a means for avoiding the complexation problem mentioned above, U.S. Pat. No. 3,985,876, proposes the use of water-miscible organic solvents to solubilize sulfonamides in combinations of sulfonamides and sulfonamide potentiators (e.g., trimethoprim).

SUMMARY OF THE INVENTION

A principal objective of the present invention is the provision of a method for preparing aqueous pharmaceutical compositions containing trimethoprim and sodium sulfacetamide in a manner such that the aqueous solubility of trimethoprim is increased substantially and the formation of insoluble complexes of trimethoprim and sodium sulfacetamide is avoided.

The provision of aqueous pharmaceutical compositions containing a synergistic combination of trimethoprim and sodium sulfacetamide based on this method of preparation represents another objective of this invention. The provision of such compositions for ophthalmic and otic use represents a specific objective of the present invention.

The foregoing objectives and other general objectives are achieved by the provision of a method for preparing aqueous pharmaceutical compositions containing therapeutic concentrations of trimethoprim and sodium sulfacetamide, which method comprises combining the sodium sulfacetamide with the trimethoprim to form a water soluble complex, whereby the aqueous solubility of trimethoprim is substantially increased.

DESCRIPTION OF THE PREFERRED EMBODIMENTS

The present invention is directed to the provision of an improved method of preparing aqueous pharmaceutical compositions containing a synergistic combination of trimethoprim and sodium sulfacetamide, and the provision of pharmaceutical compositions prepared based on this method, particularly aqueous ophthalmic and otic compositions. Trimethoprim and sodium sulfacetamide are well known compounds. The structure of trimethoprim and its method of preparation are described in U.S. Pat. No. 2,909,522, for example; the entire contents of this patent are hereby incorporated by reference in the present specification. Similarly, sodium sulfacetamide, which is also known as N-acetylsulfanilamide, is described in U.S. Pat. No. 2,411,495, for example; the entire contents of this patent are hereby incorporated by reference in the present specification. Reference is made to the Merck Index, Tenth Edition (1983) and the publications cited therein for further details concerning these compounds.

Trimethoprim is known to potentiate the antimicrobial activity of sulfonamides, as pointed out above. However, it is also known that trimethoprim has poor aqueous solubility and frequently forms insoluble complexes with sulfonamides. U.S. Pat. No. 3,985,873, proposes the use of mono salts of trimethoprim (e.g., trimethoprim hemisulfate monohydrate) as a solution to this complexation problem in connection with ophthalmic solutions containing a combination of such salts with sodium sulfacetamide and polymixins.

The present invention is based on the very surprising discovery that sodium sulfacetamide does not form an insoluble complex with trimethoprim and actually improves the aqueous solubility of trimethoprim under certain critical conditions. The principal condition critical to achieving this very surprising result is maintenance of a pH in the range of from about 6.0 to 6.5 subsequent to mixing of sodium sulfacetamide and trimethoprim in aqueous media. It has been found that insoluble complexes of sodium sulfacetamide and trimethoprim are formed if the pH of the aqueous media is outside of this mildly acidic range.

The interaction which occurs between trimethoprim and sodium sulfacetamide at this critical pH is not totally understood, but it appears that this interaction can be accurately characterized as either an association or complexation. However, it is clear that this interaction results in an improvement in the aqueous solubility of trimethoprim, which is quite surprising in light of the prior art teaching that these substances would tend to form insoluble complexes.

The aqueous preparations of the present invention are particularly well-suited for ophthalmic or otic use, but could also find other applications. These preparations are prepared by combining trimethoprim with sodium sulfacetamide in aqueous media and immediately adjusting the pH of the aqueous media to a pH in the range 6.0 to 6.5, if necessary (i.e., if the pH is not already in this range). The concentration of trimethoprim in such compositions will typically be in the range of from about 0.05% to about 1.0% (w/v), preferably 0.15% to 0.5% (w/v), and the concentration of sodium sulfacetamide will typically be in the range of from about 1.0% to about 30.0% (w/v). A preferred composition of the present invention contains 0.15% (w/v) of trimethoprim and 3.0% (w/v) of sodium sulfacetamide.

The aqueous pharmaceutical compositions of the present invention exhibit synergistic antimicrobial activity against most of the known types of pathogens (i.e., bacteria) associated with ophthalmic and otic infections. This activity is apparent when the ratio of trimethoprim to sodium sulfacetamide is in the range of 1:2 to 1:160. The greatest degree of synergy has been found to occur with ranges of 1:10 to 1:40; ratios within this range are therefore preferred.

The aqueous compositions prepared according to the present invention may also include one or more ingredients conventionally found in ophthalmic or otic formulations, such as preservatives (e.g., benzalkonium chloride or thimerosal), viscosity-imparting agents (e.g., polyvinyl alcohol or hydroxypropylmethylcellulose), and tonicity agents (e.g., sodium chloride or mannitol). The compositions will normally also include a buffering agent to maintain the pH of the solution within the above-cited critical range; hydrochloric acid or sodium hydroxide will typically be used for this purpose.

The following examples are presented to further illustrate certain preferred embodiments of the present invention, and should not be interpreted as limiting the scope of the invention in any way.

EXAMPLE 1

Four solutions saturated with trimethoprim and containing varying concentrations of sodium sulfacetamide (i.e., 0–1.4 wt. %) were prepared by placing these substances in a phosphate buffer having a pH of 6.0 and a temperature of 25° C. As shown by the data presented in Table 1 below, the addition of sodium sulfacetamide to these solutions resulted in dramatic increases in the solubility of trimethoprim.

TABLE 1

Increase in Concentration of Saturated Trimethoprim (TMP) With the Addition of Sodium Sulfacetamide at pH 6.0, 25° C.

| Concentration of Sodium Sulfacetamide (Wt. %) | Concentration of Saturated TMP (Wt. %) | % Increase in TMP Concentration |
|---|---|---|
| 0 | 0.28 | — |
| 0.4 | 0.60 | 213 |
| 0.8 | 0.66 | 233 |
| 1.4 | 0.75 | 269 |

EXAMPLE 2

Aqueous Solutions and Suspensions

Aqueous ophthalmic solutions and suspensions, which include a synergistic bactericidal combination of sodium sulfacetamide and trimethoprim as principal active ingredients, may be prepared using a formulation similar or identical to the one shown for illustration below.

| Ingredient | Amount (Wt. %) |
|---|---|
| Sulfacetamide Sodium, USP | 3.0% |
| Trimethoprim Base, USP | 0.15% |
| Sodium Thiosulfate, USP | 0.5% |
| Tyloxapol, USP | 0.05% |
| Edetate Disodium, USP | 0.01% |
| Dextran T-70 | 0.1% |
| Hydroxyethyl Cellulose, NF | 0.2% |
| Benzalkonium Chloride | 0.01% to 10.0% |
| Monobasic Sodium Phosphate, USP | 0.14% |
| Hydrochloride Acid, NF and/or Sodium Hydroxide, NF | Adjust pH to 6.0 to 6.5 |
| Purified Water, USP | QS to adjust volume |

The above formulation may be prepared by dissolving the sodium sulfacetamide, trimethoprim, sodium thiosulfate, Tyloxapol, edetate disodium, Dextran T-70, benzalkonium chloride and monobasic sodium phosphate in approximately 65 milliliters of purified water and immediately adjusting the pH to a pH in the range 6.0 to 6.5 to form a clear solution. This solution is then filtered through a 0.22 μ pore size filter into a beaker of hydroxyethyl cellulose which has been sterilized by autoclaving. The volume is then adjusted with purified water, USP.

EXAMPLE 3

Gel System

Aqueous ophthalmic gels, which include a synergistic bactericidal combination of sodium sulfacetamide and trimethoprim as principal active ingredients, may be prepared using gel vehicles, such as carboxypolymethylene (a carboxy vinyl polymer available under the trade name Carbopol from the B. F. Goodrich Company) or ethylene maleic anhydride (available under the trade name EMA from the Monsanto Company), in combination with an appropriate preservative (e.g., thimerosal, benzalkonium chloride, 1-methyl and/or propylparaben, and chlorobutanol). An example of such a formulation is set forth below.

| Ingredient | Amount |
|---|---|
| Sulfacetamide Sodium | 3.0% |
| Trimethoprim Base | 0.15% |
| Carbopol | 3.0% |
| Chlorobutanol | 0.5% |

This formulation may be prepared as follows. First, the polymer is dispersed in water, then a basic (non-drug) agent is added, such as ammonium hydroxide, sodium hydroxide, ethanolamine or other basic compounds to provide a desired pH of from 6.0 to about 6.5. After the gel has been formed in this manner, the drugs and preservative are added.

What is claimed is:

1. An aqueous pharmaceutical composition consisting essentially of 0.15–1.0 wt.% trimethoprim and 3.0–30.0 wt.% sodium sulfacetamide, said composition having a pH range of from 6.0 to 6.5.

2. The composition of claim 1 wherein the weight ratio of trimethoprim to sodium sulfacetamide is 1:2–1:160.

3. The composition of claim 1 wherein the weight ratio of trimethoprim to sodium sulfacetamide is 1:20–1:40.

4. The composition of claim 1 wherein the concentration of trimethoprim is between 0.15 wt.% and 0.5 wt.%.

5. The composition of claim 1 wherein the concentration of trimethoprim is 0.15 wt.% and the concentration of sodium sulfacetamide is 3.0 wt.%.

* * * * *